(12) United States Patent
Cohen et al.

(10) Patent No.: US 11,965,777 B2
(45) Date of Patent: Apr. 23, 2024

(54) APPARATUS AND METHODS FOR CALIBRATING OPTICAL MEASUREMENTS

(71) Applicant: ADOM, ADVANCED OPTICAL TECHNOLOGIES LTD., Lod (IL)

(72) Inventors: Yoel Cohen, Nes Ziona (IL); Ra'anan Gefen, Modiin-Macabim-Reut (IL); Shlomi Epstein, Jerusalem (IL); Yoel Arieli, Jerusalem (IL)

(73) Assignee: Adom, Advanced Optical Technologies LTD., Lod (IL)

( * ) Notice: Subject to any disclaimer, the term of this patent is extended or adjusted under 35 U.S.C. 154(b) by 577 days.

(21) Appl. No.: 17/276,265

(22) PCT Filed: Jul. 4, 2019

(86) PCT No.: PCT/IL2019/050749
§ 371 (c)(1),
(2) Date: Mar. 15, 2021

(87) PCT Pub. No.: WO2020/053847
PCT Pub. Date: Mar. 19, 2020

(65) Prior Publication Data
US 2022/0034716 A1    Feb. 3, 2022

(30) Foreign Application Priority Data
Sep. 16, 2018 (IL) .......................... 261815

(51) Int. Cl.
*G01J 3/02* (2006.01)
*A61B 3/00* (2006.01)
(Continued)

(52) U.S. Cl.
CPC .......... *G01J 3/0297* (2013.01); *A61B 3/0008* (2013.01); *A61B 3/107* (2013.01); *G01J 3/45* (2013.01)

(58) Field of Classification Search
CPC ......... G01J 3/0297; G01J 3/45; A61B 3/0008; A61B 3/107; A61B 3/101; G01B 9/02072
(Continued)

(56) References Cited

U.S. PATENT DOCUMENTS

2004/0263861 A1* 12/2004 Rafac .................... G01J 3/0205
356/519
2006/0287596 A1* 12/2006 Johnson ............... A61B 8/0825
600/437
(Continued)

FOREIGN PATENT DOCUMENTS

WO        2015132788        9/2015

*Primary Examiner* — Mohammed A Hasan
(74) *Attorney, Agent, or Firm* — Niels Haun; Dann, Dorfman, Herrell & Skillman, P.C.

(57) ABSTRACT

Apparatus and methods are described for calibrating an optical system that is used for measuring optical properties of a portion of a subjects body. During a calibration stage, a front surface of a calibration object (300) is illuminated, light reflected from a plurality of points on the calibration object (300) is detected, and intensities of the light reflected from the plurality of points on the calibration object (300) are measured. During a measurement stage, the portion of the subjects body is illuminated, and light reflected from the portion of the subjects body is detected. Measurements performed upon the light that was reflected from the portion of the subjects body are calibrated, using the measured intensities of the light reflected from the plurality of points on the calibration object (300). Other applications are also described.

19 Claims, 6 Drawing Sheets

(51) Int. Cl.
*A61B 3/107* (2006.01)
*G01J 3/45* (2006.01)

(58) Field of Classification Search
USPC .......................................................... 351/221
See application file for complete search history.

(56) References Cited

U.S. PATENT DOCUMENTS

2013/0293842 A1* 11/2013 Grenon .............. G01B 11/0625
  359/584
2014/0152958 A1* 6/2014 Okamoto ............... A61B 3/103
  351/246
2016/0338585 A1 11/2016 Arieli

* cited by examiner

APPARATUS AND METHODS FOR CALIBRATING OPTICAL MEASUREMENTS

CROSS-REFERENCE TO RELATED APPLICATIONS

The present application is a US national phase of International Application PCT/IL2019/050749 to Cohen (published as WO 20/053847), filed Jul. 4, 2019, which claims priority from Israeli Patent Application 261815, filed Sep. 16, 2018, entitled "Apparatus and methods for calibrating optical measurements," which is incorporated herein by reference.

FIELD OF EMBODIMENTS OF THE INVENTION

Some applications of the present invention generally relate to optical methods and apparatus. Specifically, some applications of the present invention relate to apparatus and methods for calibrating optical measurements, such as, spectral reflectance measurements.

BACKGROUND

Optical measurement techniques such as spectral interference measurements may be used for determining optical and/or structural properties of an object, e.g., a curved object. For example, such techniques may be used to determine the thicknesses of respective layers of a multi-layered object, such as layers of an eye. Typically, in such methods, an optical system, which includes a light source and a detector, is used. When performing optical measurement techniques, the accuracy of the measurements and the interpretation thereof, is dependent upon calibrating the optical system prior to performing the measurements.

In recent years, the diagnosis of dry eye has become an important subject for ophthalmologic diagnosis. This diagnosis was conventionally performed using a vital staining test, but this test involves chemical eye drops and pain to the examinee Other tests involve the insertion of paper strips into the eye and measurements of the wetting of the strips. These and other tests are invasive and result in non-accurate evaluations of the tear film. In recent years, non-invasive, optical methods have been developed for the diagnosis of dry eye, without requiring contact with the eye. Some such methods utilize optical measurements, such as spectral interference measurements.

SUMMARY OF EMBODIMENTS

In accordance with some applications of the present invention, apparatus and methods are provided for calibrating optical measurements (such as, spectral interference measurements) that are performed upon a portion of a subject's body, e.g., a curved portion of the subject's body, such as the cornea of the subject's eye, or a different object. The aim of the calibration is to provide information relating to characteristics of the optical system, by performing reflectance measurements using an object having known reflectance characteristics. For some applications, the apparatus and methods described herein facilitate measurements being performed on a moving eye (such as an eye undergoing saccadic motion), on an eye that is disposed off-center with respect to the optical axis of the optical system, and/or an eye that has a non-spherical cornea.

For some applications, during a calibration stage, a front surface of a calibration object having known reflectance characteristics is illuminated with light from a light source of an optical system. The front surface of the calibration object is typically at least partially curved (e.g., to generally correspond to the surface of an eye). Light reflected from a plurality of points on the calibration object is typically detected, using at least one detector of the optical system. Intensities of the light reflected from the plurality of points on the calibration object are measured. For some applications, such measurements include overall intensity measurements of the reflected light. Alternatively or additionally, such measurements include measurements that are performed with respect to respective spectral components within the reflected light. For example, such intensity measurements may be performed as per-wavelength intensity measurements, and/or as per-wavelength-band intensity measurements. For some applications, during a measurement stage (e.g., a measurement stage in which optical measurements are performed upon a subject's eye), a portion of a subject's body (e.g., the subject's eye) is illuminated with light from the light source, and light reflected from the portion of the subject's body is detected, using the detector. For some applications, during the measurement stage, the portion of the subject's body is illuminated with a different light source that has the same characteristics as the light source as the light source that was used during the calibration stage, or from a different light source that is configured to exhibit the same characteristics as the light source as the light source that was used during the calibration stage. Measurements performed upon the light that was reflected from the portion of the subject's body are typically calibrated using the measured intensities of the light reflected from the plurality of points on the calibration object. Typically, the measured intensities are calibrated on a per-wavelength or a per-wavelength-band basis.

It is noted that, for some applications, a continuous region of the surface of the calibration object is illuminated, but the reflected light is received and analyzed on a point-by-point basis, or from several discrete points simultaneously. Alternatively or additionally, the surface of the object is illuminated on a point-by-point basis, or by illuminating several discrete points simultaneously. For some applications, a continuous region of the surface of the calibration object is both illuminated and sampled, e.g., using a 2D imaging device, such as a camera.

For some applications, during the calibration stage, a plurality of reference reflectance intensity measurements are measured, each of the reference reflectance intensity measurements corresponding to a respective reflection location with respect to the optical system. For example, a plurality of reference reflectance intensity measurements may be performed by measuring intensities of the light reflected from a plurality of points on a calibration object, in the manner described hereinabove. Alternatively or additionally, the calibration object may be moved to a plurality of different locations with respect to the optical system, and a plurality of reference reflectance intensity measurements may be performed by measuring intensities of the light reflected from the calibration object, while it is disposed at respective, different locations with respect to the optical system. For some applications, during the calibration stage, the calibration object is moved in three dimensions. That is to say that the object is moved along the optical axis (the z-axis), and is also moved to respective different locations within the plane that is perpendicular to the optical axis (the x-y plane). (In the present application, the term z-axis is used to refer to the optical axis of the optical system, and the x-y plane is used to denote the plane that is perpendicular to the optical axis, as is common in the art.) A plurality of reference reflectance intensity measurements are performed by measuring intensities of the light reflected from the calibration object, while it is disposed at respective, different locations with respect to the optical system in three-dimensional space. In this manner, calibration measurements are obtained at a plurality of locations within 3D space.

During the measurement stage, the subject's eye is illuminated with light from the light source, and the disposition of the subject's eye relative to the optical system is determined. Light reflected from a point upon the subject's eye is detected using the detector, and a measurement performed upon the light that was reflected from the point upon the subject's eye is calibrated, based upon the determined disposition of the subject's eye relative to the optical system and the reference reflectance intensity measurements. Typically, the measurement performed upon the light that was reflected from the point upon the subject's eye is calibrated using the reference reflectance intensity measurement that corresponds to the location of the point upon the subject's eye relative to the optical system.

For some applications, using the above-described techniques, a model of the calibration object is developed, in which a substantial portion of the surface (e.g., more than 10 percent, more than 20 percent, or more than 30 percent of the surface), or the whole surface of the calibration object is modelled. This differs from calibration techniques that are performed with respect to only a single point upon a stationary calibration object, and which are typically performed at the center of the object. Such methods typically provide accurate calibration only at that point, such that positions that are not perfectly centered are calibrated inaccurately. Moreover, the above-described techniques can be used to provide calibration with respect to a large range of illumination angles with respect to the calibration object, such that, during the measurement stage, the calibration measurements can be used to calibrate measurements performed upon a large illumination spot size, and/or measurements performed upon sloped surfaces outside the central zone of the subject's eye. Typically, by obtaining reference reflectance intensity measurements at a plurality of reflection locations with respect to the light source of the optical system, the above-described methods provide accurate calibration when the measured object (e.g., the subject's eye) is at a plurality of locations, and at a plurality of locations upon the measured object.

In accordance with some applications of the present invention, a plurality of differently-shaped calibration objects are provided, the calibration objects having known reflectance characteristics. During a measurement stage, an input indicating a shape of the subject's eye is received. For example, a measurement may be performed by the system in order to determine the shape of the subject's eye, and/or an operator may input information regarding the shape of the subject's eye. In response to the received input, one of the calibration objects is selected as best corresponding to the shape of the subject's eye. Measurements performed on light that is reflected from the subject's eye are calibrated, using a set of intensity measurements performed on the selected calibration object, and/or on a selected location of the selected calibration object. In this manner, accurate calibration is provided even in cases in which a subject's eye is shaped non-spherically, for example, conically (e.g., in a patient suffering from keratoconus), or with a flattened region at its center (e.g., in a patient who has undergone refractive surgery). For some applications, such techniques are performed when performing measurements upon a subject's eye upon which refractive surgery has been performed.

For some applications, the calibration object has a front surface that is at least partially curved (e.g., such as to correspond to a shape of an eye), and a back surface that is configured to have a lower reflectance than the front surface, such that a ratio of a reflectance of the front surface to the reflectance of the back surface is greater than 10:1. For example, the back surface may be blackened, may be configured to have other anti-reflective properties, and/or may be configured to scatter incident light in a non-specular manner, e.g., by having a roughened or non-smooth surface. Typically, in this manner, the contribution of uncontrolled back surface reflected light rays to calibration measurements is reduced relative to the situation where the back surface reflectance is more similar to that of the front surface.

For some applications, calibration of the optical system is performed in the following manner Calibration measurements are performed upon the optical system in 3D space, using a technique as described hereinabove. Subsequently, periodic or continuous spectral-variation calibration measurements are performed, in order to account for spectral variations in the light emitted by the light source over time, by (a) directing light from the light source toward a reference object (which is not necessarily the same as the calibration object that was used for the original calibration measurements), (b) detecting light reflected from a single point upon the reference object, using the detector (e.g., the camera, or the spectrometer), and (c) comparing spectral characteristics of the light reflected from the single point to one or more intensity measurements that were performed when performing the 3D calibration measurements. In this manner, time variations in characteristics of the light source, the detector and/or another component of the optical system may be accounted for, without requiring a full calibration in 3D space to be performed each time the spectral-variation calibration measurements are made.

For some applications, the spectral-variation calibration measurements are performed prior to measurements being performed on each new subject, or on each new body portion (e.g., each new eye). Alternatively or additionally, the spectral-variation calibration measurements are performed at fixed time intervals, while the optical system is running. For example, the spectral-variation calibration measurements may be performed at fixed time intervals of between once every minute and once every 30 minutes (e.g., at intervals of between once every minute and between once every 10 minutes). Further alternatively or additionally, the spectral-variation calibration measurements are performed substantially continuously. Typically, measurements are performed on a subject within a given time period of spectral-variation calibration measurements having been performed, e.g., within one hour, within 15 minutes, or within 5 minutes of spectral-variation calibration measurements having been performed.

With respect to all intensity measurements that are described as being performed (both in the calibration stage and in the measurement stage), the measurements are typically performed with respect to respective spectral components within the reflected light. For example, such intensity measurements may be performed as per-wavelength intensity measurements, and/or as per-wavelength-band intensity measurements. Typically, respective per-wavelength intensity measurements that are acquired at the measurement stage are calibrated with respect to the corresponding per-wavelength intensity measurements that were acquired at the calibration stage. Further typically, respective per-wavelength-band intensity measurements that are acquired at the measurement stage are calibrated with respect to the corresponding per-wavelength-band intensity measurements that were acquired at the calibration stage.

There is therefore provided, in accordance with some applications of the present invention, a method for calibration of an optical system used for measuring optical properties of a portion of a body of a subject, the method including:

during a calibration stage:
illuminating a front surface of a calibration object having known reflectance characteristics with light from a light source of the optical system, the front surface being at least partially curved;
detecting light reflected from a plurality of points on the calibration object, using at least one detector of the optical system;
measuring intensities of the light reflected from the plurality of points on the calibration object; and during a measurement stage:
illuminating the portion of the subject's body with light from the light source;
detecting light reflected from the portion of the subject's body, using the at least one detector; and
calibrating measurements performed upon the light that was reflected from the portion of the subject's body, using the measured intensities of the light reflected from the plurality of points on the calibration object.

In some applications, illuminating the front surface of the calibration object with light from the light source of the optical system includes illuminating the front surface of the calibration object with light from the light source of the optical system, the calibration object further including a back surface that is configured to have a lower reflectance that the front surface, such that a ratio of a reflectance of the front surface to the reflectance of the back surface is greater than 10:1.

In some applications,
the method further includes, during the measurement stage:
receiving an input indicating a shape of the portion of the subject's body; and
selecting one calibration object out of a plurality of differently-shaped calibration objects as best corresponding to the shape of the portion of the subject's body, and
measuring intensities of the light reflected from the plurality of points on the calibration object includes measuring intensities of the light reflected from the plurality of points on the selected calibration object.

In some applications, the method further includes during the measurement stage, determining a disposition of the portion of the subject's body relative to the optical system, and calibrating measurements performed upon the light that was reflected from the portion of the subject's body includes calibrating measurements performed upon the light that was reflected from the portion of the subject's body, based upon the determined disposition of the portion of the subject's body relative to the optical system and the intensities of the light reflected from the plurality of points on the calibration object that were measured during the calibration stage.

In some applications:
the portion of the subject's body includes a cornea of an eye of the subject;
the curvature of the front surface of the calibration object corresponds to a curvature of the cornea;
illuminating the portion of the subject's body with light from the light source includes illuminating the subject's cornea with light from the light source;
detecting light reflected from the portion of the subject's body using the at least one detector includes detecting light reflected from the subject's cornea using the at least one detector; and
calibrating measurements performed upon the light that was reflected from the portion of the subject's body using the measured intensities of the light reflected from the plurality of points on the calibration object includes calibrating measurements performed upon the light that was reflected from the subject's cornea using the measured intensities of the light reflected from the plurality of points on the calibration object.

In some applications:
measuring intensities of the light reflected from the plurality of points on the calibration object includes measuring respective intensities of a plurality of wavelengths of light reflected from the plurality of points on the calibration object
detecting light reflected from the portion of the subject's body using the at least one detector includes detecting respective wavelengths of light reflected from the portion of the subject's body; and
calibrating measurements performed upon the light that was reflected from the portion of the subject's body, using the measured intensities of the light reflected from the plurality of points on the calibration object includes calibrating respective wavelengths of light that were reflected from the portion of the subject's body using the measured intensities of the respective corresponding wavelengths of light reflected from the plurality of points on the calibration object.

In some applications:
measuring intensities of the light reflected from the plurality of points on the calibration object includes measuring respective intensities of a plurality of wavelength-bands of light reflected from the plurality of points on the calibration object;
detecting light reflected from the portion of the subject's body using the at least one detector includes detecting respective wavelength-bands of light reflected from the portion of the subject's body; and
calibrating measurements performed upon the light that was reflected from the portion of the subject's body, using the measured intensities of the light reflected from the plurality of points on the calibration object includes calibrating respective wavelength-bands of light that were reflected from the portion of the subject's body using the measured intensities of the respective corresponding wavelength-bands of light reflected from the plurality of points on the calibration object.

In some applications,
the method further includes, during the calibration stage, moving the calibration object to a plurality of locations with respect to the optical system;
illuminating the front surface of the calibration object with light from the light source of the optical system includes illuminating the front surface of the calibration object with light from the light source of the optical system, while the calibration object is at each of the plurality of locations;
detecting light reflected from the plurality of points on the calibration object, using the at least one detector of the optical system includes detecting light reflected from the plurality of points on the calibration object, using the at least one detector of the optical system while the calibration object is at each of the plurality of locations; and measuring intensities of the light reflected from the plurality of points on the calibration object includes measuring intensities of the light reflected from the plurality of points on the calibration object, while the calibration object is at each of the plurality of locations.

In some applications, moving the calibration object to the plurality of locations with respect to the optical system includes moving the calibration object to a plurality of locations along an optical axis of the optical system.

In some applications, moving the calibration object to the plurality of locations with respect to the optical system includes moving the calibration object to a plurality of locations with respect to a plane that is perpendicular to an optical axis of the optical system.

In some applications, moving the calibration object to the plurality of locations with respect to the optical system includes moving the calibration object to a plurality of locations along an optical axis the optical system, and to a plurality of locations with respect to a plane that is perpendicular to the optical axis of the optical system.

In some applications, the method further includes, during the measurement stage, determining a disposition of the portion of the subject's body relative to the optical system, calibrating measurements performed upon the light that was reflected from the portion of the subject's body includes calibrating measurements performed upon the light that was reflected from the portion of the subject's body, based upon the determined disposition of the portion of the subject's body relative to the optical system and the intensities of the light reflected from the plurality of points on the calibration object that were measured during the calibration stage.

In some applications, the method further includes:
during the calibration stage acquiring one or more reference intensity measurements using a reference calibration object; and
subsequent to the calibration stage, performing periodic spectral-variation calibration measurements, in order to account for spectral variations in the light emitted by the light source over time, by:
directing light from the light source toward the reference calibration object;
detecting light reflected from the reference calibration object, using the at least one detector; and
comparing spectral characteristics of the light reflected from the reference calibration object to the one or more reference intensity measurements.

In some applications, performing periodic spectral-variation calibration measurements includes performing periodic spectral-variation calibration measurements at a time interval of at least one every 30 minutes.

In some applications, performing periodic spectral-variation calibration measurements includes performing periodic spectral-variation calibration measurements each time the measurement stage is performed with respect to a new body portion of a subject.

In some applications, performing periodic spectral-variation calibration measurements includes performing periodic spectral-variation calibration measurements each time the measurement stage is performed with respect to a new subject.

In some applications, the light source includes a broadband light source, and performing the periodic spectral-variation calibration measurements, in order to account for spectral variations in the light emitted by the light source over time includes performing periodic spectral-variation calibration measurements, in order to account for spectral variations in the light emitted by the broadband light source over time.

In some applications, the light source includes a broadband light source that is configured to emit light within a range of 400 nm to 1,000 nm, and performing the periodic spectral-variation calibration measurements, in order to account for spectral variations in the light emitted by the light source over time includes performing periodic spectral-variation calibration measurements, in order to account for spectral variations in the light emitted by the broadband light source over time.

There is further provided, in accordance with some applications of the present invention, apparatus including:
an optical system configured for measuring optical properties of a portion of a body of a subject, the optical system including a light source, and at least one detector;
a calibration object that defines a front surface that is at least partially curved, and that has known reflectance characteristics; and
at least one computer processor configured:
during a calibration stage:
to detect light from the light source that is reflected from a plurality of points on the calibration object, using the at least one detector, and
to measure intensities of the light reflected from the plurality of points on the calibration object, and
during a measurement stage:
to detect light from the light source that is reflected from the portion of the subject's body, using the at least one detector, and
to calibrate measurements of the light that was reflected from the portion of the subject's body, using the measured intensities of the light reflected from the plurality of points on the calibration object.

In some applications, the calibration object includes a back surface that is configured to have a lower reflectance that the front surface, such that a ratio of a reflectance of the front surface to the reflectance of the back surface is greater than 10:1.

In some applications:
the computer processor is further configured, during the measurement stage, to:
receive an input indicating a shape of the portion of the subject's body, and
select one calibration object out of a plurality of differently-shaped calibration
objects as best corresponding to the shape of the portion of the subject's body, and
the computer processor is configured to measure intensities of the light reflected from the plurality of points on the calibration object by measuring intensities of the light reflected from the plurality of points on the selected calibration object.

In some applications:
the computer processor is further configured, during the measurement stage, to determine a disposition of the portion of the subject's body relative to the optical system, and the computer processor is configured to calibrate measurements performed upon the light that was reflected from the portion of the subject's body, based upon the determined disposition of the portion of the subject's body relative to the optical system and the intensities of the light reflected from the plurality of points on the calibration object that were measured during the calibration stage.

In some applications:
the portion of the subject's body includes a cornea of an eye of the subject;
the curvature of the front surface of the calibration object corresponds to a curvature of the cornea; and
the computer processor is configured, during the measurement stage:
  to detect light from the light source that is reflected from the subject's cornea, using the at least one detector, and
  to calibrate measurements of the light that was reflected from the subject's cornea, using the measured intensities of the light reflected from the plurality of points on the calibration object.

In some applications, the computer processor is configured:
during the calibration stage, to measure respective intensities of a plurality of wavelengths of light reflected from the plurality of points on the calibration object, and
during the measurement stage, to:
  detect respective wavelengths of light reflected from the portion of the subject's body; and
  calibrate respective wavelengths of light that were reflected from the portion of the subject's body using the measured intensities of the respective corresponding wavelengths of light reflected from the plurality of points on the calibration object.

In some applications, the computer processor is configured:
during the calibration stage, to measure respective intensities of a plurality of wavelength-bands of light reflected from the plurality of points on the calibration object, and
during the measurement stage, to:
  detect respective wavelength-bands of light reflected from the portion of the subject's body; and
  calibrate respective wavelength-bands of light that were reflected from the portion of the subject's body using the measured intensities of the respective corresponding wavelength-bands of light reflected from the plurality of points on the calibration object.

In some applications, the computer processor is configured, during the calibration stage:
  to detect light reflected from the plurality of points on the calibration object, using the at least one detector of the optical system by detecting light reflected from the plurality of points on the calibration object, using the at least one detector of the optical system, while the calibration object is at each of a plurality of locations with respect to the optical system, and
  to measure intensities of the light reflected from the plurality of points on the calibration object by measuring intensities of the light reflected from the plurality of points on the calibration object, while the calibration object is at each of the plurality of locations.

In some applications, the computer processor is configured, during the calibration stage:
  to detect light reflected from the plurality of points on the calibration object, using the at least one detector of the optical system by detecting light reflected from the plurality of points on the calibration object, using the at least one detector of the optical system while the calibration object is at each of a plurality of locations along an optical axis of the optical system, and
  to measure intensities of the light reflected from the plurality of points on the calibration object by measuring intensities of the light reflected from the plurality of points on the calibration object, while the calibration object is at each of the plurality of locations.

In some applications, the computer processor is configured, during the calibration stage:
  to detect light reflected from the plurality of points on the calibration object, using the at least one detector of the optical system by detecting light reflected from the plurality of points on the calibration object, using the at least one detector of the optical system while the calibration object is at each of a plurality of locations with respect to a plane that is perpendicular to an optical axis of the optical system, and
  to measure intensities of the light reflected from the plurality of points on the calibration object by measuring intensities of the light reflected from the plurality of points on the calibration object, while the calibration object is at each of the plurality of locations.

In some applications, the computer processor is configured, during the calibration stage:
  to detect light reflected from the plurality of points on the calibration object, using the at least one detector of the optical system by detecting light reflected from the plurality of points on the calibration object, using the at least one detector of the optical system while the calibration object is at each of a plurality of locations along an optical axis of the optical system, and with respect to a plane that is perpendicular to the optical axis of the optical system, and
  to measure intensities of the light reflected from the plurality of points on the calibration object by measuring intensities of the light reflected from the plurality of points on the calibration object, while the calibration object is at each of the plurality of locations.

In some applications, the computer processor is configured, during the measurement stage, to:
  determine a disposition of the portion of the subject's body relative to the optical system, and
  calibrate measurements performed upon the light that was reflected from the portion of the subject's body by calibrating measurements performed upon the light that was reflected from the portion of the subject's body, based upon the determined disposition of the portion of the subject's body relative to the optical system and the intensities of the light reflected from the plurality of points on the calibration object that were measured during the calibration stage.

In some applications, the computer processor is further configured:
  during the calibration stage, to acquire one or more reference intensity measurements using a reference calibration object, and
  subsequent to the calibration stage, to perform periodic spectral-variation calibration measurements, in order to account for spectral variations in the light emitted by the light source over time, by:

detecting light generated by the light source that is reflected from the reference calibration object, using the at least one detector; and comparing spectral characteristics of the light reflected from the reference calibration object to the one or more reference intensity measurements.

In some applications, the computer processor is configured to perform the periodic spectral-variation calibration measurements by performing periodic spectral-variation calibration measurements at a time interval of at least one every 30 minutes.

In some applications, the computer processor is configured to perform the periodic spectral-variation calibration measurements by performing periodic spectral-variation calibration measurements each time the measurement stage is performed with respect to a new body portion of a subject.

In some applications, the computer processor is configured to perform the periodic spectral-variation calibration measurements by performing periodic spectral-variation calibration measurements each time the measurement stage is performed with respect to a new subject.

In some applications, the light source includes a broadband light source, and the computer processor is configured to perform the periodic spectral-variation calibration measurements, in order to account for spectral variations in the light emitted by the broadband light source over time.

In some applications, the light source includes a broadband light source that is configured to emit light within a range of 400 nm to 1,000 nm.

There is further provided, in accordance with some applications of the present invention, a method for use with an eye of a subject, the method including:

during a calibration stage, measuring a plurality of reference reflectance intensity measurements using at least one detector of an optical system, each of the reference reflectance intensity measurements corresponding to a respective reflection location with respect to the optical system; and during a measurement stage:
illuminating the subject's eye with light from the light source;
determining a disposition of the subject's eye relative to the optical system;
detecting light reflected from a point upon the subject's eye using the at least one detector; and
calibrating a measurement performed upon the light that was reflected from the point upon the subject's eye, based upon the determined disposition of the subject's eye relative to the optical system and the reference reflectance intensity measurements.

In some applications, measuring a plurality of reference reflectance intensity measurements includes moving a calibration object to a plurality of locations with respect to the optical system and acquiring respective reference reflectance intensity measurements, while the calibration object is disposed at each of the plurality of locations.

In some applications:
measuring the plurality of reference reflectance intensity measurements includes measuring respective intensities of a plurality of wavelengths of light for each of the respective reflection locations;
detecting light reflected from point upon the subject's eye using the at least one detector includes detecting respective wavelengths of light reflected from point upon the subject's eye; and
calibrating a measurement performed upon the light that was reflected from the point upon the subject's eye, based upon the determined disposition of the subject's eye relative to the optical system and the reference reflectance intensity measurements includes calibrating respective wavelengths of light that were reflected from the point upon the subject's eye using the measured intensities of the respective corresponding wavelengths of light detected for the reflection location corresponding to the disposition of the subject's eye.

In some applications:
measuring the plurality of reference reflectance intensity measurements includes measuring respective intensities of a plurality of wavelength-bands of light for each of the respective reflection locations;
detecting light reflected from point upon the subject's eye using the at least one detector includes detecting respective wavelength-bands of light reflected from point upon the subject's eye; and
calibrating a measurement performed upon the light that was reflected from the point upon the subject's eye, based upon the determined disposition of the subject's eye relative to the optical system and the reference reflectance intensity measurements includes calibrating respective wavelength-bands of light that were reflected from the point upon the subject's eye using the measured intensities of the respective corresponding wavelength-bands of light detected for the reflection location corresponding to the disposition of the subject's eye.

In some applications, measuring a plurality of reference reflectance intensity measurements includes while a calibration object is disposed at a given location with respect to the optical system, and acquiring respective reference reflectance intensity measurements from respective points upon a surface of the calibration object.

There is further provided, in accordance with some applications of the present invention, apparatus for use with an eye of a subject, the apparatus including:

an optical system including a light source, and at least one detector;

at least one computer processor configured:
during a calibration stage to measure a plurality of reference reflectance intensity measurements using the at least one detector, each of the reference reflectance intensity measurements corresponding to a respective reflection location with respect to the optical system, and
during a measurement stage:
to determine a disposition of the subject's eye relative to the optical system,
to detect light generated by the light source that is reflected from a point upon the subject's eye, using the at least one detector, and
to calibrate a measurement performed upon the light that was reflected from the point upon the subject's eye, based upon the determined disposition of the subject's eye relative to the optical system and the reference reflectance data.

In some applications, the computer processor is configured:
during the calibration stage, to measure respective intensities of a plurality of wavelengths of light for each of the respective reflection locations; and
during the measurement stage:
to detect respective wavelengths of light reflected from point upon the subject's eye; and
to calibrate respective wavelengths of light that were reflected from the point upon the subject's eye using the measured intensities of the respective corresponding wavelengths of light detected for the reflection location corresponding to the disposition of the subject's eye.

In some applications, the apparatus is configured for use with a calibration object, and the computer processor is configured to measure the plurality of reference reflectance intensity measurements by the calibration object being moved to a plurality of locations with respect to the optical system the computer processor acquiring respective reference reflectance intensity measurements, while the calibration object is disposed at each of the plurality of locations.

In some applications, the apparatus is configured for use with a calibration object, and the computer processor is configured to measure the plurality of reference reflectance intensity measurements by acquiring respective reference reflectance intensity measurements from respective points upon a surface of the calibration object, while the calibration object is disposed at a given location with respect to the optical system.

There is further provided, in accordance with some applications of the present invention, the following inventive concepts:

Inventive concept 1. Apparatus for measuring optical properties of an eye of a subject, the apparatus comprising:
   an optical system comprising a light source, and at least one detector;
   a plurality of differently-shaped calibration objects, the calibration objects having known reflectance characteristics; and
   at least one computer processor configured, during a measurement stage:
      to detect light generated by the light source that is reflected from the subject's eye, using the at least one detector,
      to receive an input indicating a shape of the subject's eye,
      in response to the received input, to select one of the calibration objects as best corresponding to the shape of the subject's eye; and
      to calibrate measurements performed on the light that was reflected from the subject's eye, using a set of intensity measurements performed on the selected calibration object.

Inventive concept 2. The apparatus according to inventive concept 1, wherein:
   prior to the measurement stage, the computer processor is configured to perform a calibration stage, in which the computer processor is configured:
      to detect light generated by the light source that is reflected from each of the calibration objects, using at least one detector of the optical system, and
      to perform respective sets of intensity measurements on the light reflected from each of the calibration objects, and
   during the measurement stage, the computer processor is configured to calibrate measurements performed on the light that was reflected from the subject's eye, using the set of intensity measurements that were performed on the selected calibration object during the calibration stage.

Inventive concept 3. The apparatus according to inventive concept 1, wherein, subsequent to the computer processor receiving an input indicating the shape of the subject's eye, the computer processor is configured to perform calibration measurements upon the selected calibration object, by:
   detecting light generated by the light source that is reflected from the selected calibration object, using the at least one detector of the optical system, and
   performing intensity measurements on the light reflected from the selected calibration object.

Inventive concept 4. A method for measuring optical properties of an eye of a subject using an optical system, the method comprising, during a measurement stage:
   illuminating the subject's eye with light from a light source of the optical system;
   detecting light reflected from the subject's eye using at least one detector of the optical system;
   selecting one of a plurality of differently-shaped calibration objects as best corresponding to the shape of the subject's eye; and
   calibrating measurements that are performed on the light that was reflected from the subject's eye, using a set of intensity measurements performed on the selected calibration object.

Inventive concept 5. The method according to inventive concept 4, wherein calibrating measurements that are performed on the light that was reflected from the subject's eye, using the set of intensity measurements performed on the selected calibration object comprises:
   prior to the measurement stage, performing a calibration stage, by:
      illuminating front surfaces of each of the calibration objects with light from the light source;
      detecting light reflected from each of the calibration objects, using at least one detector of the optical system; and
      performing respective sets of intensity measurements on the light reflected from each of the calibration objects; and
   during the measurement stage, calibrating measurements performed on the light that was reflected from the subject's eye, using the set of intensity measurements that were performed on the selected calibration object during the calibration stage.

Inventive concept 6. The method according to inventive concept 4, wherein calibrating measurements that are performed on the light that was reflected from the subject's eye, using the set of intensity measurements performed on the selected calibration object comprises, subsequent to selecting one of the plurality of differently-shaped calibration objects as best corresponding to the shape of the subject's eye, performing calibration measurements upon the selected calibration object, by:
   illuminating a front surface of the selected calibration object, with light from the light source,
   detecting light reflected from the selected calibration object, using the at least one detector of the optical system, and
   performing intensity measurements on the light reflected from the selected calibration object.

Inventive concept 7. Apparatus for use with an optical system for performing measurements on an eye of a subject, the apparatus comprising:
   a calibration object that is configured to facilitate optical calibration of the optical system, the calibration object having known reflectance characteristics, and being shaped to define:
      a front surface that is at least partially curved; and
      a back surface, the back surface being configured to have a lower reflectance that the front surface, such that a ratio of a reflectance of the front surface to the reflectance of the back surface is greater than 10:1.

Inventive concept 8. A method for use with an optical system for performing measurements on an eye of a subject, the method comprising:
performing calibration measurements on the optical system by:
directing light from a light source of the optical system toward a calibration object having known reflectance characteristics, and that is shaped to define:
a front surface that is at least partially curved, and
a back surface, the back surface being configured to have a lower reflectance that the front surface, such that a ratio of a reflectance of the front surface to the reflectance of the back surface is greater than 10:1,
detecting light reflected from the calibration object, using at least one detector of the optical system; and
performing intensity measurements on the light reflected from the calibration object.

Inventive concept 9. A method for use with an optical system for performing measurements, the method comprising:
performing calibration measurements on the optical system in 3D space by:
directing light from a light source of the optical system toward at least one calibration object that has known reflectance characteristics;
detecting light reflected from a plurality of points upon the at least one calibration object, using at least one detector of the optical system; and
performing intensity measurements on the reflected light; and
subsequently, performing periodic spectral-variation calibration measurements, in order to account for spectral variations in the light emitted by the light source over time, by:
directing light from the light source toward a calibration object;
detecting light reflected from a single point upon the calibration object, using the at least one detector; and
comparing spectral characteristics of the light reflected from the single point to one or more intensity measurements that were performed when performing the 3D calibration measurements.

Inventive concept 10. The method according to inventive concept 9, wherein performing periodic spectral-variation calibration measurements comprises performing periodic spectral-variation calibration measurements at a time interval of at least once every 30 minutes.

Inventive concept 11. The method according to inventive concept 9, wherein performing periodic spectral-variation calibration measurements comprises performing periodic spectral-variation calibration measurements each time measurements are performed with respect to a new body portion of a subject.

Inventive concept 12. The method according to inventive concept 9, wherein performing periodic spectral-variation calibration measurements comprises performing periodic spectral-variation calibration measurements each time measurements are performed with respect to a new subject.

Inventive concept 13. The method according to any one of inventive concepts 9-12, wherein the light source includes a broadband light source, and wherein performing the periodic spectral-variation calibration measurements, in order to account for spectral variations in the light emitted by the light source over time comprises performing periodic spectral-variation calibration measurements, in order to account for spectral variations in the light emitted by the broadband light source over time.

Inventive concept 14. The method according to inventive concept 13, wherein the light source includes a broadband light source that is configured to emit light within a range of 400 nm to 1,000 nm, and wherein performing the periodic spectral-variation calibration measurements, in order to account for spectral variations in the light emitted by the light source over time comprises performing periodic spectral-variation calibration measurements, in order to account for spectral variations in the light emitted by the broadband light source over time.

Inventive concept 15. Apparatus for use with an optical system for performing optical measurements the optical system including a light source and at least one detector, the apparatus comprising:
at least one calibration object; and
at least one computer processor configured:
to perform 3D calibration measurements on the optical system by:
detecting light generated by the light source that is reflected from a plurality of points upon at least one calibration object, using the at least one detector of the optical system, and
performing intensity measurements on the reflected light, and
subsequently, to periodically perform spectral-variation calibration measurements, in order to account for spectral variations in the light emitted by the light source over time, by:
detecting light generated by the light source that is reflected from a single point upon a calibration object, using the at least one detector; and
comparing spectral characteristics of the light reflected from the single point to one or more intensity measurements that were performed when performing the 3D calibration measurements.

Inventive concept 16. The apparatus according to inventive concept 15, wherein the computer processor is configured to perform the periodic spectral-variation calibration measurements at a time interval of at least once every 30 minutes.

Inventive concept 17. The apparatus according to inventive concept 15, wherein the computer processor is configured to perform the periodic spectral-variation calibration measurements each time measurements are performed with respect to a new body portion of a subject.

Inventive concept 18. The apparatus according to inventive concept 15, wherein the computer processor is configured to perform the periodic spectral-variation calibration measurements each time measurements are performed with respect to a new subject.

Inventive concept 19. The apparatus according to any one of inventive concepts 15-18, wherein the light source comprises a broadband light source, and wherein the computer processor is configured to perform the periodic spectral-variation calibration measurements, in order to account for spectral variations in the light emitted by the broadband light source over time.

Inventive concept 20. The apparatus according to inventive concept 19, wherein the light source comprises a broadband light source that is configured to emit light within a range of 400 nm to 1,000 nm.

The present invention will be more fully understood from the following detailed description of embodiments thereof, taken together with the drawings, in which:

DETAILED DESCRIPTION OF EMBODIMENTS

Figure 1:
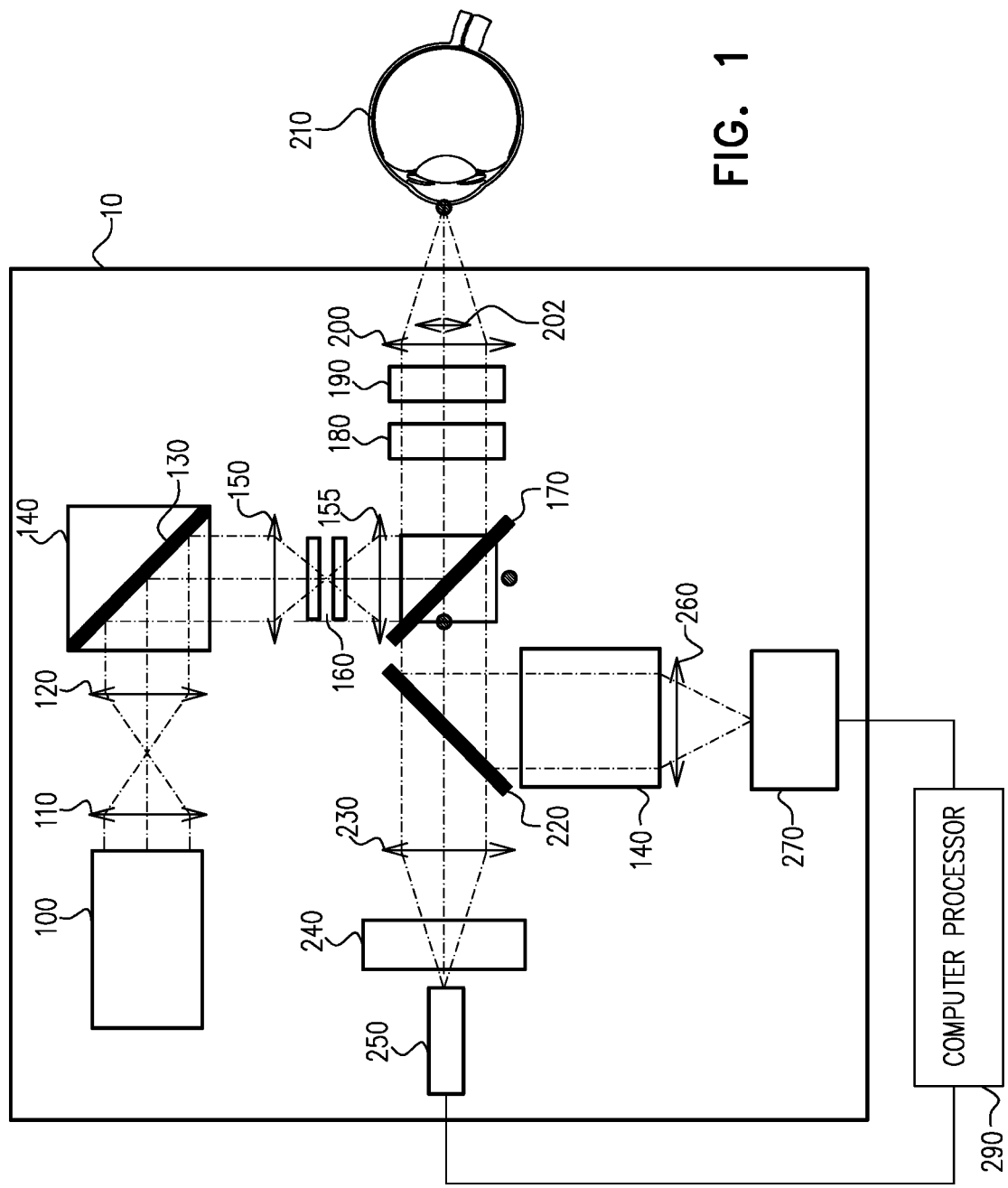
FIG. 1 is a schematic illustration of an optical system for performing measurements upon a portion of a subject's body, in accordance with some applications of the present invention.

Reference is now made to FIG. 1, which is a schematic illustration of an optical system 10 for performing optical measurements upon a portion of a subject's body or a different measured object, in accordance with some applications of the present invention. Typically, optical system 10 is used to measure a biological tissue or a biological substance, such as the cornea of an eye 210 of a subject or a different portion of the subject's body, over a large area. For some applications, the substructure of the subject's tear film is measured, including structural measurements of the lipid layer, the aqueous layer, the mucin layer, and/or microvilli.

It is noted that optical system as shown in FIG. 1 is provided by way of example. However, the scope of the present application includes applying the apparatus and techniques described herein for performing calibration of an optical system to any optical system that includes a light source and a detector and that is configured to measure the optical properties of an object, such as a curved object.

For some applications, optical system 10 includes a plurality of detectors, such as one or more color cameras 270 and one or more spectrometers 250. For some applications, the optical system includes a plurality of spectrometers. For some applications, camera 270 includes a hyperspectral camera. For some applications, the optical system includes an interferometer 140. Typically, along an illumination path of the optical system, light is emitted from a light source 100. Light source 100 is typically a broadband light source a light source configured to emit light at a range of 350-1,250 nm, e.g., 400-1,000 nm, e.g., 500-900 nm). Further typically, the light is collimated by lenses 110 and 120. For some applications, the tight is bent by a mirror 130. In some applications, mirror 130 comprises a moveable mirror of interferometer 140, and interferometer 140 is disposed along the illumination path. Alternatively or additionally, interferometer 140 is disposed along an imaging path of the optical system, as described in further detail hereinbelow. (It is noted that FIG. 1 shows interferometer 140 disposed in both the illumination path and in the imaging path. However, typically, the interferometer is disposed in either the illumination path, or the imaging path.) The light is focused by a lens 150 onto at least two grids 160. The light is then collimated by a lens 155, and is passed through a beam-splitter 170, such as to form two split beams of lights. One of the beams of light is directed toward a cornea of a subject's eye 210 using a focusing optical element 200 (e.g., a lens). In the above-described manner, grids 160 are imaged onto the subject's cornea. Typically, grids 160 are used for autofocusing and positioning the cornea at a given distance from a portion of the optical system, by examining the sharpness of the images of the grids on the cornea. Optionally, other optical elements 180 are disposed in the light path, such as a polarizer, which can contribute toward proper background removal. A reticle 190 may also be disposed within the light path to serve as a target for directing the subject's gaze.

The reflected light is gathered by the central part of the focusing optical element 200 or by an additional optical element 202 placed in the central part of the focusing optical element 200. Typically, along an imaging path of the optical system, the gathered reflected light passes back through beam splitter 170. For some applications, at least a portion of the reflected light then proceeds through a focusing element 230 (e.g., a lens) and the focusing element focuses the reflected tight onto spectrometer 250. For some applications, the portion of the reflected light passes through a deflecting element 240, prior to being detected by the spectrometer. Alternatively or additionally, at least a portion of the reflected light proceeds through a focusing element 260 (e.g., a lens) and the focusing element focuses the reflected light onto color camera 270. For example, as shown, a portion of the reflected light may be bent by mirror and/or beam splitter 220, and directed to color camera 270 via focusing element 260. For some applications, the reflected light passes through interferometer 140 along the imaging path. For example, as shown, the portion of the reflected light that is directed toward color camera 270 may be directed to the color camera, via the interferometer. For some applications, the reflected light is combined with the second split beam of light that was formed by beam splitter 170.

Typically, a characteristic of the imaged object (e.g., cornea of eye 210) is determined by performing optical measurements (e.g., spectral interference measurements) upon the reflected light detected by spectrometer 250. For some applications, a combination of measurements is measured using data obtained by color camera 270, as well as data obtained by spectrometer 250, e.g., using techniques as described in US 2016/0338585 to Arieli, which is incorporated herein by reference.

It is again noted that optical system 10 as shown in FIG. 1 is an illustrative example of an optical system that may be used in conjunction with the calibration techniques and apparatus described herein. However, the scope of the present invention includes applying the calibration techniques and apparatus described herein to an optical system that differs from that shown in FIG. 1, whether in terms of certain components of the optical system, or the general structure of the optical system. As noted hereinabove, the scope of the present application includes applying the apparatus and techniques described herein for performing calibration of an optical system to any optical system that eludes a light source and a detector (e.g., one or more spectrometers and/or one or more cameras) and that is configured to measure the optical properties of an object, such as a curved object.

In order to attain accurate optical measurements (e.g., spectral interference measurements) relating to the object (e.g., the cornea of eye 210), a calibration process is typically performed in order to obtain calibration measurements with reference to which measurements that are performed upon the object may be calibrated. The aim of the calibration process is to provide information relating to characteristics of the optical system, by performing reflectance measurements using an object having known reflectance characteristics. For some applications, such measurements include overall intensity measurements of the light reflected from the object. Alternatively or additionally, such measurements include measurements that are performed with respect to respective spectral components within the light reflected from the object.

Accordingly, in a separate stage from performing measurements upon the light reflected from the object ("the measurement stage"), a calibration stage is performed. During the calibration stage, a calibration object (e.g., calibration object 300, shown in FIG. 2) is used to calibrate the optical system. The calibration object typically defines a front surface that is shaped in a similar shape to that of the object that is measured. For example, if subject's cornea is to be measured, a calibration object having a front surface that is at least partially curved is typically used. For some applications, a calibration object having a different shape that corresponds to the shape of a subject's cornea is used, as described in further detail hereinbelow. Typically, the calibration object has known reflectance characteristics. Therefore, measurements of light that is reflected from the calibration object provides information regarding characteristics of the optical system, with reference to which the measurements that are performed upon the measured object may be calibrated.

For some applications, during the calibration stage, a front surface of the calibration object is illuminated with light from light source 100 of optical system 10. Light reflected from a plurality of points on the calibration object is typically detected, using at least one detector of the optical system (e.g., spectrometer 250, and/or camera 270). Intensities of the light reflected from the plurality of points on the calibration object are measured (e.g., using computer processor 290). For some applications, such measurements include overall intensity measurements of the reflected light. Alternatively or additionally, such measurements include measurements that are performed with respect to respective spectral components within the reflected light. For example, such intensity measurements may be performed as per-wavelength intensity measurements, and/or as per-wavelength-band intensity measurements. It is noted that, for some applications, a continuous region of the surface of the calibration object is illuminated, but the reflected light is received and analyzed on a point-by-point basis, or from several discrete points simultaneously. Alternatively or additionally, the surface of the object may be illuminated on a point-by-point basis, or by illuminating several discrete points simultaneously. For some applications, a continuous region of the surface of the calibration object is both illuminated and sampled, for example, using a 2D imaging device, such as camera 270.

For some applications, during a measurement stage (e.g., a measurement stage in which spectral interference measurements are performed upon a subject's eye), a portion of a subject's body (e.g., the subject's eye) is illuminated with light from the light source, and light reflected from the portion of the subject's body is detected, using the detector. Measurements performed upon the light that was reflected from the portion of the subject's body are typically calibrated using the measured intensities of the light reflected from the plurality of points on the calibration object. Typically, respective per-wavelength intensity measurements that are acquired at the measurement stage are calibrated with respect to the corresponding per-wavelength intensity measurements that were acquired at the calibration stage. Further typically, respective per-wavelength-band intensity measurements that are acquired at the measurement stage are calibrated with respect to the corresponding per-wavelength-band intensity measurements that were acquired at the calibration stage.

For some applications, during the calibration stage, a plurality of reference reflectance intensity measurements are measured, each of the reference reflectance intensity measurements corresponding to a respective reflection location with respect to the optical system. For example, a plurality of reference reflectance intensity measurements may be performed by measuring intensities of the light reflected from a plurality of points on the calibration object, in the manner described hereinabove. Alternatively or additionally, the calibration object may be moved to plurality of different locations with respect to the optical system, and a plurality of reference reflectance intensity measurements may be performed by measuring intensities of the light reflected from the calibration object, while it is disposed at respective locations with respect to the optical system. For some applications, during the calibration stage, the calibration object is moved in three dimensions. That is to say that the object is (a) moved along the optical axis (the z-axis), as described with reference to FIG. 5 for example, and (b) is also moved to respective different locations within the plane that is perpendicular to the optical axis (the x-y plane), as described with reference to FIG. 4 for example. A plurality of reference reflectance intensity measurements are performed by measuring intensities of the light reflected from the calibration object, while it is disposed at respective, different locations with respect to the optical system in three-dimensional space. In this manner, calibration measurements are obtained at a plurality of location within 3D space.

During the measurement stage, the subject's eye is illuminated with light from the light source, and a disposition of the subject's eye relative to the optical system is determined. Light reflected from a point upon the subject's eye is detected using the detector, and a measurement performed upon the light that was reflected from the point upon the subject's eye is calibrated, based upon the determined disposition of the subject's eye relative to the optical system and the reference reflectance intensity measurements. Typically, the measurement performed upon the light that was reflected from the point upon the subject's eye is calibrated using the reference reflectance intensity measurement that corresponds to the location of the point upon the subject's eye relative to the optical system.

By way of illustration and not limitation, the disposition of the subject's eye within the x-y plane may be determined by placing a ring around the objective lens of the optical system, such that the center of the ring is coincident with the optical axis of the optical system. The ring casts a shadow upon the measured object (e.g., the subject's eye), and the disposition of the object with respect to the shadow of the ring is used to determine the location of the object within the x-y plane, relative to the optical axis of the optical system. Alternatively or additionally, the disposition of the object with respect to reticle 190 may be used to determine the location of the object within the x-y plane, relative to the optical axis of the optical system. Again, by way of illustration and not limitation, the disposition of the object along the optical axis of the optical system may be determined by examining the sharpness of the images of grids 160 on the measured object, as described, hereinabove, with reference to FIG. 1. Typically, the disposition of the calibration object (during the calibration stage), as well as the disposition of the eye (during the measurement stage) is determined by the computer processor, for example, using the above-described techniques.

For some applications, measurements that are performed upon the calibration object are used to calibrate the optical system in the following manner. An appropriate model for the reflection coefficient of the object is used that describes the interaction of the illumination path of the optical system and the imaging path of the optical system with the calibration object. Such a model typically includes the relationship between the illumination ray angles and the location at which they are incident upon the calibration object. An integral over all angles with the known reflectance of the calibration object is used to determine the absolute reflection coefficient, and therefore the accurate value of calibration, at each location upon the calibration object. For example, this may be achieved by ray tracing optics. It should be noted that each angle, each wavelength has its own weight factor due to the optical transmission factor of the system. The reflection coefficient $R(\theta, \varphi, \lambda)$ of the object itself can be calculated by any electromagnetic wave simulation known in the art. Accordingly, the overall reflection coefficient at a certain point (x, y) for a discrete number of rays of a certain wavelength $\lambda$, is:

$$R_{x,y,\lambda} = \sum_{j=1}^{n} \sum_{i=1}^{m} R_{x,y}(\varphi_j, \theta_i, \lambda)$$

Or for the continuous case $$R_{x,y,\lambda} = \int_{\theta_1}^{\theta_2} \int_{\varphi_1}^{\varphi_2} R_{x,y}(\varphi, \theta, \lambda) d\varphi \sin\theta d\theta$$

Where $\theta_1, \theta_2, \varphi_1, \varphi_2$ denote the minimum and maximum angles of detected rays.

Figure 2:
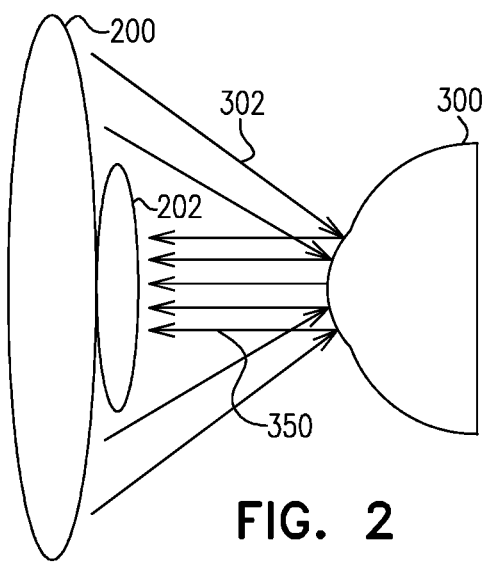
FIG. 2 is a schematic illustration of apparatus for performing calibration measurements upon a calibration object that is centered with respect to the optical axis of the optical system, in accordance with some applications of the present invention.

Reference is now made to FIG. 2, which is a schematic illustration of a calibration object 300 and a portion of optical system 10, the calibration object being centered with respect to the optical axis of optical system 10. Typically, the calibration process includes several calibration light intensity measurements, in order to cover the whole surface of the calibration object. As shown in FIG. 2, for some applications focusing element 200 has a high numerical aperture, such that the calibration object is illuminated by a fan of incident light rays 302 that encompass a large angle. The reflected light rays 350 are collected by optical element 202 and relayed to a detector of the optical system (e.g., spectrometer 250 and/or color camera 270). In this way each location on the object has different rays 350 configured at slightly different orientations, and which will therefore have different calibration coefficients. The intensity of the light received by the detector is analyzed by computer processor 290 associated with the optical system (shown in FIG. 1).

Figure 3A:
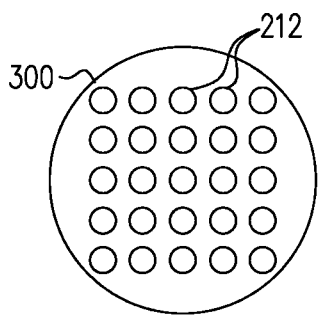
FIGS. 3A, 3B, 3C, 3D, 3E, and 3F are schematic illustrations of a calibration object, a plurality of points of which have been illuminated with respective patterns of illumination points, and/or a plurality of points of which having respective patterns have been measured, in accordance with some applications of the present invention.
Figure 3B:
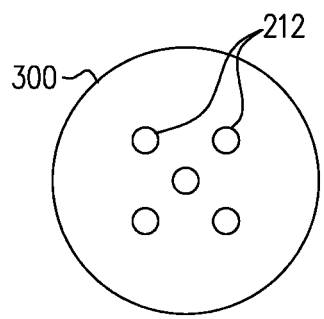
Figure 3C:
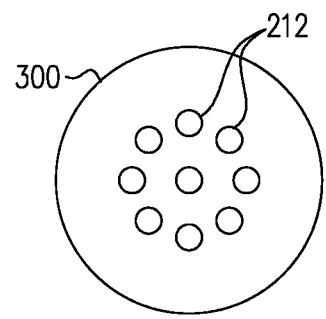
Figure 3D:
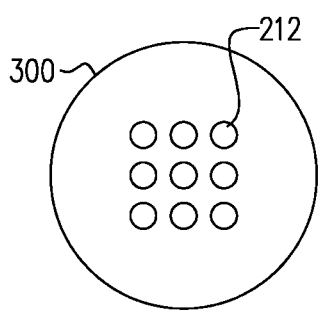
Figure 3E:
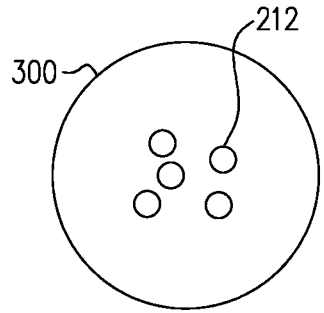
Figure 3F:
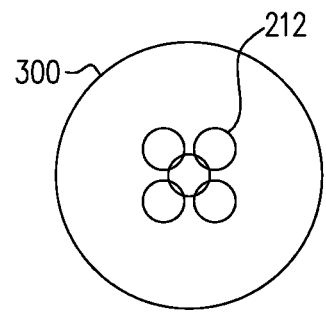

References is now made to FIGS. 3A, 3B, 3C, 3D, 3E, and 3F, which are schematic illustrations of calibration object 300, a plurality of points of which have been illuminated with respective patterns of illumination points, and/or a plurality of points of which having respective patterns have been measured, in accordance with some applications of the present invention. Typically, in order to achieve calibration at different locations upon the calibration object, an arrangement (e.g., a grid arrangement) of points of light 212 is spanned over the surface of the calibration object. The spacing between the points may have any pattern, such as a large rectangle (FIG. 3A), a quincunx (FIG. 3B), circular (FIG. 3C), a small rectangle (FIG. 3D), random (FIG. 3E), and/or overlapping (FIG. 3F). The reflected light rays from the object are either imaged one by one using a detector, such as spectrometer 250, or are imaged simultaneously using a 2D detector, such as camera 270. The measured intensity of the reflected light at each is used to calibrate the optical system at that point. For some applications, the grid of points of light is moved over the surface of the calibration object. Alternatively or additionally, the calibration object is moved to a plurality of locations with respect to the light source of the optical system, and reflected light is received from the calibration object at the plurality of locations. After illuminating a plurality of points and receiving the reflected light, the whole surface of the calibration object is typically modelled using interpolation methods, in order to obtain calibration over a substantial portion of the surface of the calibration object (e.g., more than 10 percent, more than 20 percent, or more than 30 percent of the surface), or over the whole surface of the calibration object.

Typically, the points upon the surface of the calibration object that are illuminated are spread arbitrarily on the calibration object's surface and it is not necessary to direct any one of the points to any particular point of the surface of the calibration object. Typically, this increases the capabilities of the calibration process, by avoiding the requirement that at the measurement stage, the location of the measured point upon the measured object (such as the cornea of the subject's eye) relative to the optical system axis will be exactly at the same location as the calibration object. Rather, it is typically the case that a plurality of reference reflectance intensity measurements are performed by measuring intensities of the light reflected from a plurality of points on a calibration object.

During the measurement stage, the subject's eye is illuminated with light from the light source, and a disposition of a given measurement point upon the subject's eye relative to the optical axis of the optical system is determined. Light reflected from a point upon the subject's eye is detected using the detector, and a measurement performed upon the light that was reflected from the point upon the subject's eye is calibrated, based upon the determined disposition of the measurement point upon the subject's eye relative to the optical axis and the reference reflectance intensity measurements. Typically, the measurement performed upon the light that was reflected from the point upon the subject's eye is calibrated using the reference reflectance intensity measurement that corresponds to the location of the point upon the subject's eye relative to the optical axis of the optical system.

With reference to FIGS. 3A-F, it is noted that, for some applications, a continuous region of the surface of the calibration object is illuminated, but the reflected light is received and analyzed on a point-by-point basis, or from several discrete points simultaneously. Alternatively or additionally, the surface of the object may be illuminated on a point-by-point basis, or by illuminating several discrete points simultaneously. For some applications, a continuous region of the surface of the calibration object is both illuminated and sampled, for example, using a 2D imaging device, such as camera 270.

Figure 4:
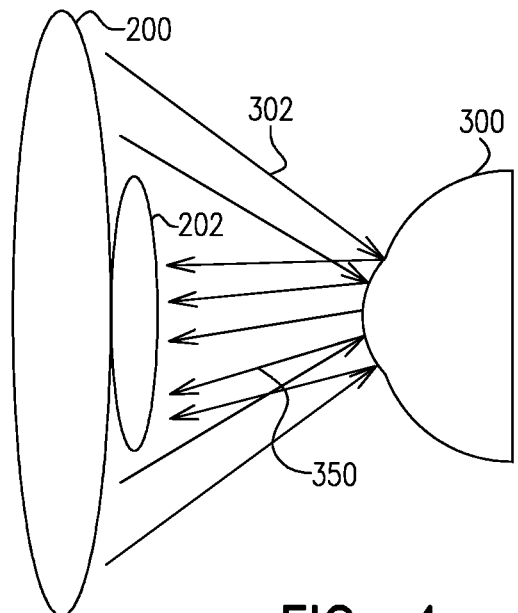
FIG. 4 is a schematic illustration of apparatus for performing calibration measurements upon a calibration object that is off-center with respect to the optical axis of the optical system, in accordance with some applications of the present invention.

Reference is now made to FIG. 4, which is a schematic illustration of apparatus for performing calibration measurements upon calibration object 300, the calibration object being off-center with respect to the optical axis of the optical system, in accordance with some applications of the present invention. The apparatus is similar to that shown in FIGS. 1 and 2, however, as shown in FIG. 4, the illumination across the surface of the calibration object is not uniform due to the calibration object being off-center with respect to the optical axis of the optical system. In such cases of non-uniform illumination, at each point, the illumination rays have different contributions and the reflectivity calculation should take this into account. Moreover, due to the curvature of its front surface, the off-center calibration object causes reflected light rays from outer peripheral areas and different angles to be collected by optical element 202. This causes the calculations of the reflectivity corresponding to each point to be altered relative to the arrangement shown in FIG. 2, in which the calibration object is centered with respect to the optical axis of the optical system.

For some applications, a full map of the calibration data in 3D space is generated (e.g., in order to account for such off-center measurements), and the relevant data for a measurement that is performed at a given location upon the object is used to calibrate the measurement. For some applications, in order to obtain reference reflectance intensity measurements, during the calibration stage, the calibration object is moved to a plurality of locations along the x-y plane and calibration measurements are performed upon the calibration object ile it is disposed at each of the locations, using the techniques described herein. Typically, when performing such techniques it is not necessary to precisely place the calibration object at a given location within the x-y plane, but it is necessary to determine the location of the calibration object within the x-y plane. Typically, computer processor 290 determines the location of the calibration object within the x-y plane and long the optical axis, e.g., using the techniques described hereinabove for determining the location of the subject's eye.

Figure 5:
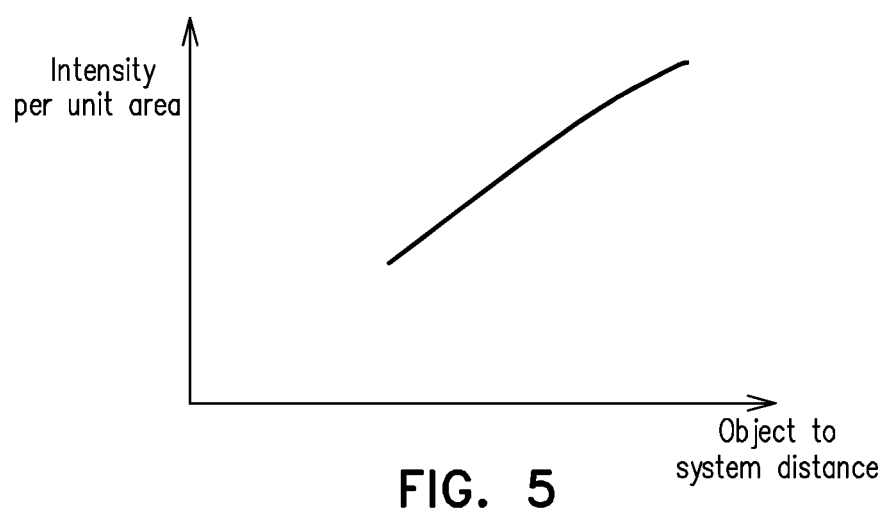
FIG. 5 is a graph showing a typical variation in intensity measurements that are performed upon an object, with respect to the distance of the object from the light source, in accordance with some applications of the present invention.

Reference is now made to FIG. 5, which is a graph showing a typical variation in intensity of light per unit area that is incident upon an object (e.g., a calibration object or a measured object, such as the cornea of the eye), with respect to the distance of the object from the light source of the optical system, in accordance with some applications of the present invention. As shown, since the illumination from the optical system is performed in converging mode such as to concentrate the light, the flux density of light (i.e., the irradiance of the light) is not constant along the optical axis, and within a given range of distances along the z-axis (i.e., along the range of distances along which the light is converging), the intensity of light that is incident upon the object increases as the object moves further from the light source. In order to account for the variation in the intensity of light that is generated upon the object as the object moves along the optical axis, typically calibration measurements are performed upon the calibration object at different locations along the optical axis. In this manner, the calibration process accounts for flux density variations along the optical axis, e.g., using a linear or a parabolic model. Subsequently, when performing measurements upon the measured object (e.g., the subject's eye), the disposition of the measured object along the optical axis is determined, and measurements that are performed upon the object are calibrated using the calibration measurements corresponding to that location along the optical axis.

Typically, in order to attain a full continuous calibration map, interpolations between the measured calibration points are performed within the x-y plane and/or along the optical axis, such that measurement points that are performed upon locations upon the measured object (e.g., the cornea of the eye) that fall between the measured calibration map points may be calibrated.

As described hereinabove, typically the complete calibration process is used to provide a plurality of a plurality of reference reflectance intensity measurements that correspond to respective locations within 3D space, inter alia, by moving the calibration object in the x, y, and z dimensions to discrete points and measuring the reflectivity of at least of one point on its surface, where the position in space of each measured point on the calibration object's surface is accurately know, either by measurement or by other means. For some applications, at least some of the reference reflectance intensity measurements are obtained using interpolation methods, as described hereinabove.

Typically, performing calibration measurements in 3D space in the above-described manner is relatively burdensome, and therefore it is desirable to perform such measurements at a relatively low frequency (e.g. approximately once a week, once a month, and/or each time the light source is replaced). However, typically there are variations in components of the optical system the light source and/or a detector, such as spectrometer 250) that take place at a greater frequency. For example, there may be intensity changes in the light source and/or gain changes in the detectors, due to temperature changes. Moreover, as described hereinabove, light source 100 is typically a broadband light source. Temperature changes typically have an impact on the relationship between the different wavelengths generated by such a light source (e.g. due to the black body radiation dependency on the temperature). That is to say that there may be variation in the spectrum of illumination that is generated by the light source over time. As described hereinabove, typically in order to obtain data relating to the structure of a subject's tear film, spectral interference measurements are performed upon the subject's cornea. For such measurements, it is important to recalibrate the system periodically in order to account for variations in the spectrum of illumination that is generated by the light source over time, as well as other variations in the optical system.

In view of the above, in accordance with some applications of the present invention, calibration measurements are performed upon the optical system in 3D space, using a technique as described hereinabove. For example, light from a light source of the optical system may be directed toward at least one calibration object that has known reflectance characteristics, and that has a curved front surface. Light reflected from a plurality of points upon the at least one calibration object is then detected, using at least one detector of the optical system, and intensity measurements are performed on the reflected light.

Subsequently, periodic spectral-variation calibration measurements are performed, in order to account for spectral variations in the light emitted by the light source over time, by (a) directing light from the light source toward a reference object, (b) detecting light reflected from a single point upon the reference object, using the detector (e.g. spectrometer and/or color camera), and (c) comparing spectral characteristics of the light reflected from the single point to one or more of the intensity measurements that were performed, when performing the 3D calibration measurements. For some applications, in steps (b) and (c) light reflected from a small number of points (rather than a single point) upon the calibration object, such as less than 5 points are detected using the detector, and spectral characteristics of the light reflected from the small number of points are compared to one or more of the intensity measurements that were performed when performing the 3D calibration measurements. In this manner, time variations in characteristics of the light source, the detector and/or another component of the optical system may be accounted for periodically, without requiring a full calibration in 3D space to be performed each time the periodic spectral-variation calibration measurements are made.

For some applications, the periodic spectral-variation calibration measurements are performed prior to measurements being performed on each new subject, or on each new body portion (e.g., each new eye). Alternatively or additionally, the spectral-variation calibration measurements are performed at fixed time intervals, while the optical system is running. For example, the spectral-variation calibration measurements may be performed at fixed time intervals of between once every minute, and once every 30 minutes (e.g., between once every minute and between once every 10 minutes). Further alternatively or additionally, the spectral-variation calibration measurements are performed substantially continuously. Typically, measurements are performed on a subject within a given time period of spectral-variation calibration measurements having been performed, e.g., within one hour, within 15 minutes, or within 5 minutes of spectral-variation calibration measurements having been performed.

For some applications, for the purpose of the performing the periodic spectral-variation calibration measurements, an optical element that is inserted and remains within the illumination path of the optical system (and/or using an existing optical element within the illumination path of the optical system) is used as the reference object. For example, a surface of beam splitter 170 that is normal to the incident light beam, which reflects a substantial amount of light to spectrometer 250 may be used. In this manner, it is not necessary to actively place a calibration object at a given location with respect to the optical system each time one of the periodic spectral-variation calibration measurements is performed. For some applications, an initial measure of the reflectance from the reference object is made during the 3D calibration measurement stage, and this is used as a reference against which future spectral-variation calibration measurements are compared.

Figure 6A:
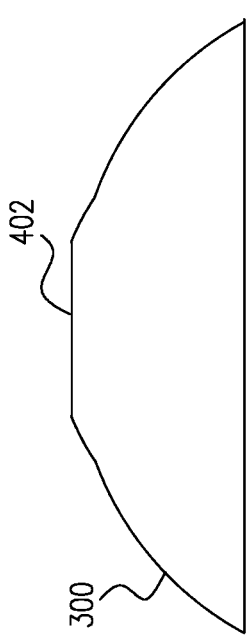
FIGS. 6A and 6B are schematic illustrations of a subject's eye that has been altered by laser surgery, such that the eye defines a flattened region at its center, and a corresponding calibration object, in accordance with some applications of the present invention.
Figure 6B:
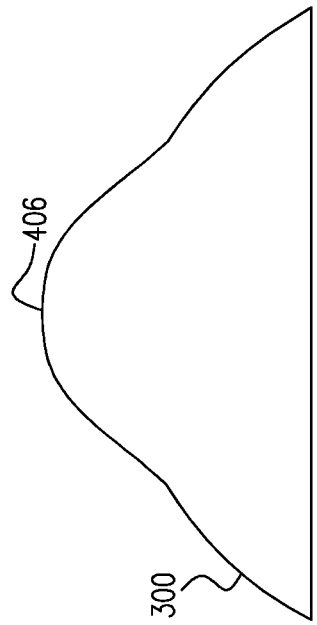
Figure 6C:
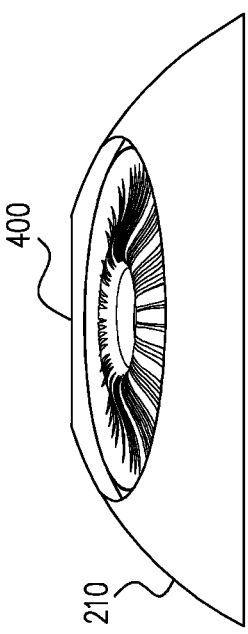
FIGS. 6C and 6D are schematic illustrations of a keratoconus subject's eye that has a cone shape at its center, and a corresponding calibration object, in accordance with some applications of the present invention.
Figure 6D:
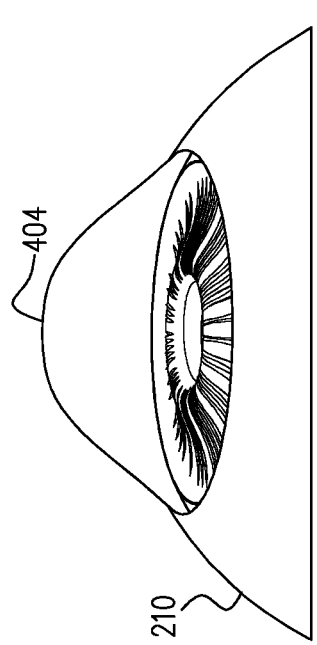

Reference is now made to FIGS. 6A and 6B, which are schematic illustrations of a subject's eye 210 that has been altered by laser surgery, such that the eye defines a flattened region 400 at its center, and a corresponding calibration object 300, in accordance with some applications of the present invention. As shown, like the eye, the calibration object has a flattened region 402 at its center. Reference is also made to FIGS. 6C and 6D, which are schematic illustrations of a keratoconus subject's eye 210 that has a cone shape 404 at its center, and a corresponding calibration object, in accordance with some applications of the present invention. As shown, like the eye, the calibration object has a conical region 406 at its center. In general, the calibration object that is used to calibrate a given measured object is typically selected to be as similar in shape to the measured object as possible. A typical eye can be approximated by a cone that transitions smoothly to a sphere towards the center. However, different eyes have different shapes. For example, eyes with keratoconus have a more emphasized conic shape, and, as described above, an eye that underwent a refractive surgery is typically such that the structure of the cornea is flat at its center.

In accordance with some applications of the present invention, a plurality of differently-shaped calibration objects are provided, the calibration objects having known reflectance characteristics. During a measurement stage, an input indicating a shape of the subject's eye is received. For example, a measurement may be performed by the system in order to determine the shape of the subject's eye, and/or an operator may input information regarding the shape of the subject's eye. In response to the received input, one of the calibration objects is selected as best corresponding to the shape of the subject's eye. Measurements performed on light that is reflected from the subject's eye are calibrated, using a set of intensity measurements performed on the selected calibration object. In this manner, accurate calibration is provided even in cases in which a subject's eye is shaped non-spherically, e.g., conically, or with a flattened region, at its center. For some applications, such techniques are performed when performing measurements upon a subject's eye upon which refractive surgery has been performed.

For some such applications, prior to the measurement stage, the calibration stage is performed, in which respective sets of intensity measurements on the light reflected from each of the differently-shaped calibration objects, and then during the measurement stage, measurements performed on the light that was reflected from the subject's eye are calibrated, using the set of intensity measurements that were performed on the selected calibration object during the calibration stage. Alternatively, subsequent to the computer processor receiving an input indicating the shape of the subject's eye, the computer processor is configured to perform calibration measurements upon the selected calibration object.

In general, the scope of the present application includes combining the calibration apparatus and methods described with reference to FIGS. 1-5 with the apparatus and methods associated with the plurality of differently-shaped calibration objects, as described with reference to FIGS. 6A-D.

Figure 7A:
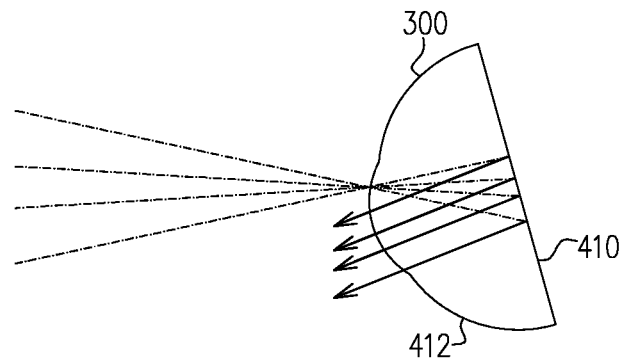
FIGS. 7A, 7B, and 7C are schematic illustrations showing the reflectance from a back surface of a calibration object, in a case in which the calibration object is illuminated with a small illumination spot and using low numerical aperture illumination (FIG. 7A), in a case in which the calibration object is illuminated with a large illumination spot and using high numerical aperture illumination (FIG. 7B), and in a case in which the calibration object is illuminated with a large illumination spot and using high numerical aperture illumination, and the reflectance of the back surface is reduced relative to that of the front surface (FIG. 7C), in accordance with some applications of the present invention.
Figure 7B:
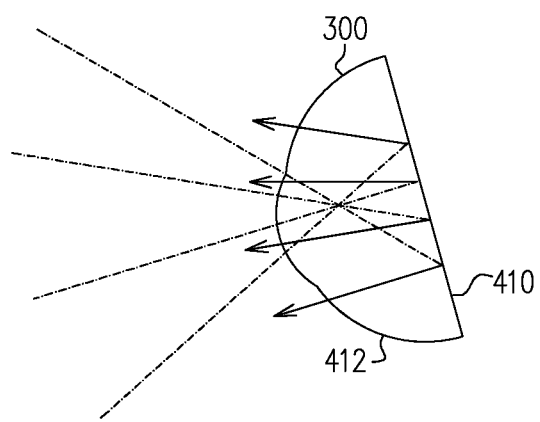
Figure 7C:
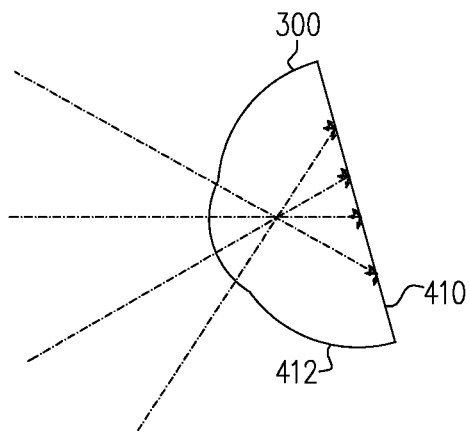

Reference is now made to FIGS. 7A, 7B, and 7C, which are schematic illustrations showing the reflectance from a back surface 410 of calibration object 300, in a case in which the calibration object is illuminated with a small illumination spot and using low numerical aperture illumination (FIG. 7A), in a case in which the calibration object is illuminated with a large illumination spot and using high numerical aperture illumination (FIG. 7B), and in a case in which the calibration object is illuminated with a large illumination spot and using high numerical aperture illumination, and the reflectance of the back surface is reduced relative to that of the front surface (FIG. 7C), in accordance with some applications of the present invention. Typically, the calibration object has a front surface 412 that is shaped to correspond to a shape of an eye, and back surface 410.

For some applications, the calibration object is illuminated with a small illumination spot and using low numerical aperture illumination, as shown in FIG. 7A. Typically though, the calibration object is illuminated with a large illumination spot and using high numerical aperture illumination (e.g., covering an angle of more than 100 degrees (e.g., approximately 120 degrees)), as shown in FIGS. 7B and 7C. As may be observed by comparing FIG. 7B to FIG. 7A, if the back surface of the object provides substantial specular reflection, then illuminating the object with a large illumination spot and using high numerical aperture illumination results in a large amount of light being reflected from the back surface over a large range of angles. Typically, due to the large angle of illumination, there is substantial specular reflection from the back surface, even if the back surface is tilted with respect to the optical axis. The reflected light from the back surface typically cannot be distinguished from the reflected light from the front surface and results in inaccurate calibration measurement being performed. Therefore, for some applications, the back surface is configured to have a lower reflectance that the front surface, e.g., such that a ratio of a reflectance of the front surface to the reflectance of the back surface is greater than 10:1. For example, the back surface of the calibration object may be covered with a black-coating that absorbs the light, may be configured to have other anti-reflective properties (e.g., by the surface being roughened), and/or may be configured to scatter incident light in a non-specular manner, as shown in FIG. 7C. Typically, in this manner, the contribution of uncontrolled back surface reflected light rays to calibration measurements is reduced relative to if the back surface reflectance were to be more similar to that of the front surface.

In general, the scope of the present application includes combining (a) the calibration apparatus and methods described with reference to FIGS. 1-5, (b) the apparatus and methods associated with the plurality of differently-shaped calibration objects, as described with reference to FIG. 6, and/or (c) the apparatus and methods associated with a using a calibration object having a back surface that has low reflectance, as described with reference to FIGS. 7A-C.

Figure 8:
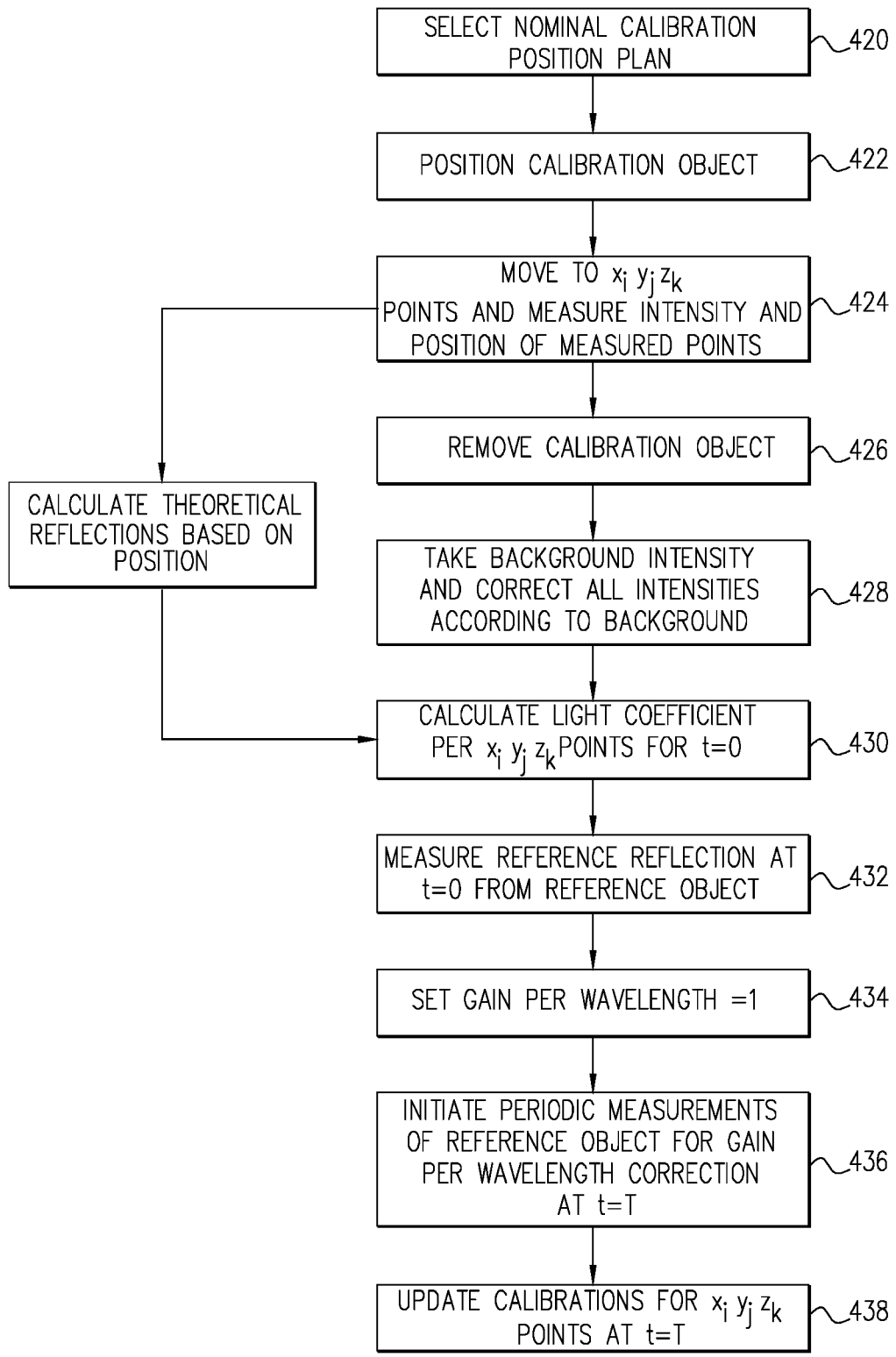
FIG. 8 is a flowchart showing steps of a calibration process that is performed, in accordance with some applications of the present invention.

Reference is now made to FIG. 8, which is a flowchart showing steps of a calibration process that is performed, in accordance with some applications of the present invention. For some applications, the calibration process includes at least some of the following steps:

Steps 420: Selection of nominal calibration position.
Step 422: Placement of calibration object at that position.
Step 424: Acquisition of data at a plurality of x/y/z positions, and measurement of those positions.
Step 426: Removal of the calibration object.
Step 428: Measurement of background light intensity and correction of all measured reflected intensities, based on background intensity.
Step 430: Calculate light coefficients by using theoretical reflections for each of the x/y/z positions.
Step 432: Measure reference reflection, for the purpose of measuring variations in the optical system over time.
Step 434: For the initial calibration in 3D space, set gain per wavelength factor to 1.
Step 436: Initiate periodic measurements in order to account for variations in the optical system over time.
Step 438: Update the calibration reference data, based upon the measured variations in the optical system.

With respect to all intensity measurements that are described as being performed (both in the calibration stage and in the measurement stage), the measurements are typically performed with respect to respective spectral components within the reflected light. For example, such intensity measurements may be performed as per-wavelength intensity measurements, and/or as per-wavelength-band intensity measurements. Typically, respective per-wavelength intensity measurements that are acquired at the measurement stage are calibrated with respect to the corresponding per-wavelength intensity measurements that were acquired at the calibration stage. Further typically, respective per-wavelength-band intensity measurements that are acquired at the measurement stage are calibrated with respect to the corresponding per-wavelength-band intensity measurements that were acquired at the calibration stage.

Applications of the invention described herein can take the form of a computer program product accessible from a computer-usable or computer-readable medium (e.g., a non-transitory computer-readable medium) providing program code for use by or in connection with a computer or any instruction execution system, such as a computer processor 290 (FIG. 1), which may be in communication with optical system 10. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 290) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that the algorithms described herein can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 290) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processor 290 is typically a hardware device programmed with computer program instructions to produce a special purpose computer. For example, when programmed to perform the algorithms described herein, computer processor 290 typically acts as a special purpose optical-system-calibration computer processor. Typically, the operations described herein that are performed by computer processor 290 transform the physical state of a memory, which is a real physical article, to have a different magnetic polarity, electrical charge, or the like depending on the technology of the memory that is used. For some applications, operations that are described as being performed by a computer processor are performed by a plurality of computer processors in combination with each other.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

In particular it should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

The invention claimed is:

1. A method for calibration of an optical system used for measuring optical properties of a portion of a body of a subject, the method comprising:
   during a calibration stage, deriving information regarding characteristics of the optical system, with reference to which the measurements that are performed upon the portion of the subject's body may be calibrated, by:
      illuminating a front surface of a calibration object having known reflectance characteristics with light from a light source of the optical system, the front surface being at least partially curved;
      detecting light reflected from a plurality of points on the calibration object, using at least one detector of the optical system;
      measuring intensities of the light reflected from the plurality of points on the calibration object; and
      determining a calibration value at each location upon the calibration object by calculating an integral over all angles with the known reflectance of the calibration object to determine the absolute reflection coefficient; and
   during a measurement stage:
      illuminating the portion of the subject's body with light from the light source;
      detecting light reflected from the portion of the subject's body, using the at least one detector; and
      calibrating measurements performed upon the light reflected from the portion of the subject's body, using the measured intensities of the light reflected from the plurality of points on the calibration object.

2. The method according to claim 1, wherein the calibration object further includes a back surface that is configured to have a lower reflectance that the front surface, such that a ratio of a reflectance of the front surface to the reflectance of the back surface is greater than 10:1.

3. The method according to claim 1,
   further comprising, during the measurement stage:
      receiving an input indicating a shape of the portion of the subject's body; and
      selecting one calibration object out of a plurality of differently-shaped calibration objects as best corresponding to the shape of the portion of the subject's body,
   wherein measuring intensities of the light reflected from the plurality of points on the calibration object comprises measuring intensities of the light reflected from the plurality of points on the selected calibration object.

4. The method according to claim 1, further comprising during the measurement stage, determining a disposition of the portion of the subject's body relative to the optical system, wherein calibrating measurements performed upon the light that was reflected from the portion of the subject's body comprises calibrating measurements performed upon the light that was reflected from the portion of the subject's body, based upon the determined disposition of the portion of the subject's body relative to the optical system and the intensities of the light reflected from the plurality of points on the calibration object as measured during the calibration stage.

5. The method according to claim 1, wherein:
   measuring intensities of the light reflected from the plurality of points on the calibration object comprises measuring respective intensities of a plurality of wavelengths of light reflected from the plurality of points on the calibration object;
   detecting light reflected from the portion of the subject's body using the at least one detector comprises detecting respective wavelengths of light reflected from the portion of the subject's body; and
   calibrating measurements performed upon the light that was reflected from the portion of the subject's body, using the measured intensities of the light reflected from the plurality of points on the calibration object comprises calibrating respective wavelengths of light that were reflected from the portion of the subject's body using the measured intensities of the respective corresponding wavelengths of light reflected from the plurality of points on the calibration object.

6. The method according to claim 1, wherein:
measuring intensities of the light reflected from the plurality of points on the calibration object comprises measuring respective intensities of a plurality of wavelength-bands of light reflected from the plurality of points on the calibration object;
detecting light reflected from the portion of the subject's body using the at least one detector comprises detecting respective wavelength-bands of light reflected from the portion of the subject's body; and
calibrating measurements performed upon the light that was reflected from the portion of the subject's body, using the measured intensities of the light reflected from the plurality of points on the calibration object comprises calibrating respective wavelength-bands of light that were reflected from the portion of the subject's body using the measured intensities of the respective corresponding wavelength-bands of light reflected from the plurality of points on the calibration object.

7. The method according to claim 1,
further comprising, during the calibration stage, moving the calibration object to a plurality of locations with respect to the optical system,
wherein:
illuminating the front surface of the calibration object with light from the light source of the optical system comprises illuminating the front surface of the calibration object with light from the light source of the optical system, while the calibration object is at each of the plurality of locations;
detecting light reflected from the plurality of points on the calibration object, using the at least one detector of the optical system comprises detecting light reflected from the plurality of points on the calibration object, using the at least one detector of the optical system while the calibration object is at each of the plurality of locations; and
measuring intensities of the light reflected from the plurality of points on the calibration object comprises measuring intensities of the light reflected from the plurality of points on the calibration object, while the calibration object is at each of the plurality of locations.

8. The method according to claim 7, wherein moving the calibration object to the plurality of locations with respect to the optical system comprises moving the calibration object to a plurality of locations along an optical axis of the optical system.

9. The method according to claim 7, wherein moving the calibration object to the plurality of locations with respect to the optical system comprises moving the calibration object to a plurality of locations with respect to a plane that is perpendicular to an optical axis of the optical system.

10. The method according to claim 7, wherein moving the calibration object to the plurality of locations with respect to the optical system comprises moving the calibration object to a plurality of locations along an optical axis the optical system, and to a plurality of locations with respect to a plane that is perpendicular to the optical axis of the optical system.

11. The method according to claim 7, further comprising during the measurement stage, determining a disposition of the portion of the subject's body relative to the optical system, wherein calibrating measurements performed upon the light that was reflected from the portion of the subject's body comprises calibrating measurements performed upon the light that was reflected from the portion of the subject's body, based upon the determined disposition of the portion of the subject's body relative to the optical system and the intensities of the light reflected from the plurality of points on the calibration object that were measured during the calibration stage.

12. The method according to claim 7, further comprising:
during the calibration stage acquiring one or more reference intensity measurements using a reference calibration object; and
subsequent to the calibration stage, performing periodic spectral-variation calibration measurements, in order to account for spectral variations in the light emitted by the light source over time, by:
directing light from the light source toward the reference calibration object;
detecting light reflected from the reference calibration object, using the at least one detector; and
comparing spectral characteristics of the light reflected from the reference calibration object to the one or more reference intensity measurements.

13. The method according to claim 12, wherein performing periodic spectral-variation calibration measurements comprises performing periodic spectral-variation calibration measurements at a time interval of at least one every 30 minutes.

14. The method according to claim 12, wherein performing periodic spectral-variation calibration measurements comprises performing periodic spectral-variation calibration measurements each time the measurement stage is performed with respect to a new body portion of a subject.

15. The method according to claim 12, wherein performing periodic spectral-variation calibration measurements comprises performing periodic spectral-variation calibration measurements each time the measurement stage is performed with respect to a new subject.

16. The method according to claim 12, wherein the light source includes a broadband light source, and wherein performing the periodic spectral-variation calibration measurements, in order to account for spectral variations in the light emitted by the light source over time comprises performing periodic spectral-variation calibration measurements, in order to account for spectral variations in the light emitted by the broadband light source over time.

17. The method according to claim 16, wherein the light source includes a broadband light source that is configured to emit light within a range of 400 nm to 1,000 nm, and wherein performing the periodic spectral-variation calibration measurements, in order to account for spectral variations in the light emitted by the light source over time comprises performing periodic spectral-variation calibration measurements, in order to account for spectral variations in the light emitted by the broadband light source over time.

18. The method according to claim 1, wherein:
the portion of the subject's body includes a cornea of an eye of the subject;
the curvature of the front surface of the calibration object corresponds to a curvature of the cornea;
illuminating the portion of the subject's body with light from the light source comprises illuminating the subject's cornea with light from the light source;
detecting light reflected from the portion of the subject's body using the at least one detector comprises detecting light reflected from the subject's cornea using the at least one detector; and
calibrating measurements performed upon the light reflected from the portion of the subject's body using the measured intensities of the light reflected from the plurality of points on the calibration object comprises calibrating measurements performed upon the light reflected from the subject's cornea using the measured intensities of the light reflected from the plurality of points on the calibration object.

19. Apparatus comprising:

an optical system configured for measuring optical properties of a portion of a body of a subject, the optical system comprising a light source, and at least one detector;

a calibration object that defines a front surface that is at least partially curved, and that has known reflectance characteristics; and at least one computer processor configured:

during a calibration stage, to derive information regarding characteristics of the optical system, with reference to which the measurements that are performed upon the portion of the subject's body may be calibrated, by:

detecting light from the light source that is reflected from a plurality of points on the calibration object, using the at least one detector, measuring intensities of the light reflected from the plurality of points on the calibration object, and determining a calibration value at each location upon the calibration object by calculating an integral over all angles with the known reflectance of the calibration object to determine the absolute reflection coefficient, and during a measurement stage:

to detect light from the light source that is reflected from the portion of the subject's body, using the at least one detector, and to calibrate measurements of the light that was reflected from the portion of the subject's body, using the measured intensities of the light reflected from the plurality of points on the calibration object.

* * * * *